United States Patent [19]
Paquette et al.

[11] 4,432,223
[45] Feb. 21, 1984

[54] FOOTWEAR TESTING APPARATUS AND METHOD

[75] Inventors: Elmer G. Paquette; Michael J. Maloney, both of Madison, Wis.; Douglas S. Swain, Brockton; Richard F. LaCerte, Hudson, both of Mass.; James B. Peters, Madison; Robert E. Mast, Dalton, both of Wis.

[73] Assignee: The United States of America as represented by the Secretary of the Army, Washington, D.C.

[21] Appl. No.: 405,672

[22] Filed: Aug. 6, 1982

[51] Int. Cl.³ .................... G01M 3/00; G01M 19/00; G01N 3/56
[52] U.S. Cl. ........................................... 73/7; 73/73; 73/432.1
[58] Field of Search ................................ 73/7, 432 V

[56] References Cited

U.S. PATENT DOCUMENTS

| | | | |
|---|---|---|---|
| 658,547 | 9/1900 | Kennedy | 73/7 |
| 4,130,007 | 12/1978 | Hayashi | 73/7 |

Primary Examiner—S. Clement Swisher
Attorney, Agent, or Firm—Robert P. Gibson; Anthony T. Lane; Lawrence E. Labadini

[57] ABSTRACT

Footwear is tested and evaluated by apparatus which is capable of simulating the actual wearing thereof under various environmental conditions. The apparatus includes a leg pylon and artificial foot which are moved as a unit by apparatus which duplicates the motion of the knee and ankle of an individual. The artificial foot, on which the footwear to be tested is mounted, may be provided with various sensors or condition simulators.

10 Claims, 6 Drawing Figures

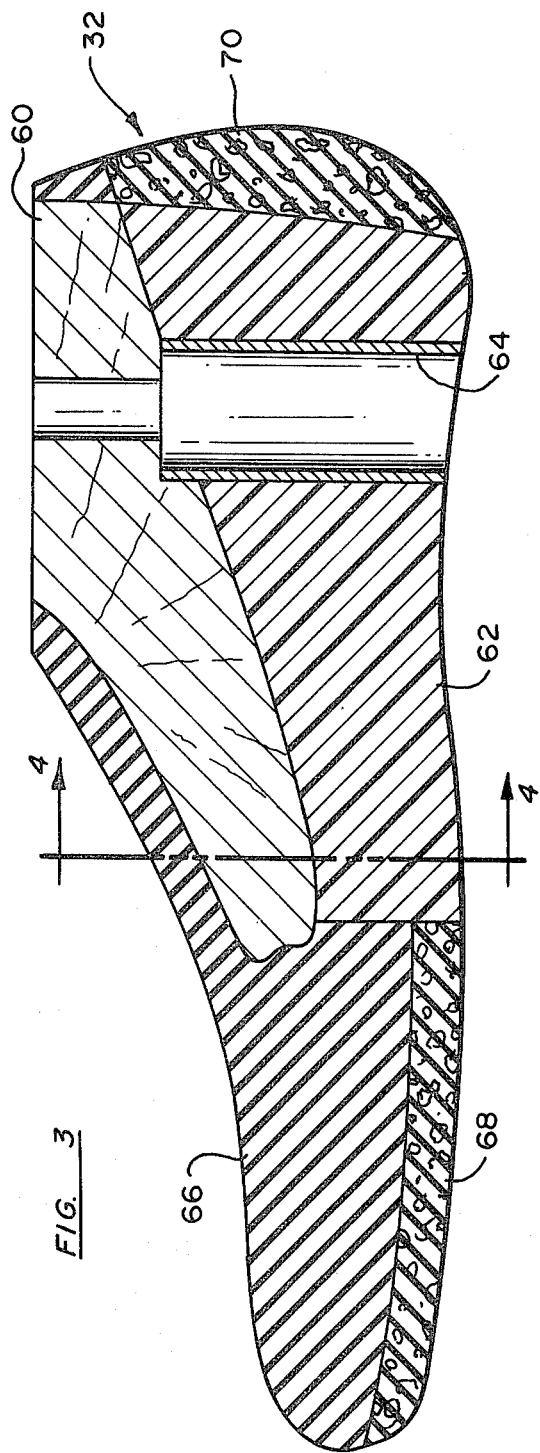
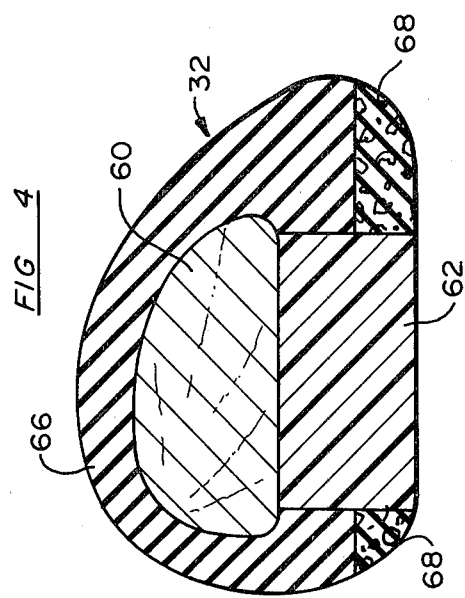

FOOTWEAR TESTING APPARATUS AND METHOD

BACKGROUND OF THE INVENTION (1) Field of the Invention

The present invention relates to the testing of footwear and particularly to the evaluation of characteristics such as water repellency and cold intrusion of footwear. More specifically, this invention is directed to a footwear testing device capable of simulating the kinematic action of a walking individual under various environmental conditions. Accordingly, the general objects of the present invention are to provide novel and improved methods and apparatus of such character.

(2) Description of the Prior Art

The science of footwear research undoubtedly dates from the beginning of man's use of animal skins and other materials for foot protection. As different materials were tried and different methods of attaching them to the feet were developed, differences in performance were observed. Those materials and designs which proved to be the most comfortable and convenient, and provided the best protection, were studied, copied and improved upon. This technique of making and subsequently testing prototypes is, as will be explained in greater detail below, still widely used. Thus, considering the testing of footwear for use by military personnel, until recently much of the testing was performed by volunteers under actual or simulated field conditions. This type of testing is costly, inaccurate with respect to some of the parameters of interest and not suitable for those tests, shock absorption capability for example, which could expose the wearer to the risk of injury.

Among the characteristics of footwear which desirably should be evaluated are water repellency, cold intrusion, sole and heel wear, heat-loss, and shock absorption. A high degree of moisture repellency is extremely important since dry footwear is more comfortable to the wearer and greatly reduces the incidence of many types of foot disorder. Similarly, the ability to keep the foot warm is a characteristic of importance. As is well known, cold injury to feet is a problem which has affected military campaigns throughout history. It is difficult to evaluate factors such as water repellency and cold intrusion through the use of wear-type tests because of the subjective nature of such tests. For example, most individuals are unable to detect small amounts of moisture entering their footwear and when moisture is detected they are unable to provide an exact location.

Foot injuries are, of course, a serious problem in industry and in the military. Accordingly, footwear is continually being redesigned, tested and updated to include recent technological advances which provide additional protection. The tests to be performed include measurement of the cushioning/shock absorbing characteristics of the footwear and, as noted above, these characteristics can not be measured by wear-testing. In the prior art a "falling dart" test has frequently been used to measure the shock absorbing characteristics of a boot or shoe. These tests employ an impactor which is dropped onto the insole of the shoe and an accelerometer which measures the change in acceleration resulting from the impactor striking the shoe. Shoes are normally tested in the rear foot (heel) and forefoot (ball) areas. Such "falling dart" tests are not entirely satisfactory since they frequently necessitate cutting away part of the shoe under test in order to allow the impactor to enter and such removal of material from any structural portion of a boot or shoe will significantly alter is performance. Further, falling dart impactors are poor replicates of the human foot and, since shoes normally conform to the shape of the wearer's foot, a flat or hemispherical impactor may not provide an adequate presentation of the cushioning characteristics which would actually be experienced by the foot. Also, a "falling dart" test will only measure the characteristic of a new shoe and impact absorption is known to change as a result of use. It would be extremely desirable to have the means of determining how rapidly the degree of protection afforded by the footwear under test would deteriorate in actual use.

It has also been proposed to employ strain gages attached to the legs of an individual walking or running on a treadmill and/or transducers located in the shoe under test to test for shock absorption characteristics. The major disadvantages of these approaches is that they require the use of human subjects and highly skilled technicians both of which greatly increase the cost of testing.

The advantages incident to replacing wear-testing employing human volunteers with a machine are numerous and obvious. However, the mechanisms required to duplicate the movements of the human's foot during walking are quite complex. The human foot is compressed of twenty-six (26) separate bones wraped in a mixture of muscles, ligaments, fat and calluses. The duplication of such a complex structure would be nearly impossible. This fact has contributed to the prior failure to provide footwear testing equipment capable of measuring the parameters of interest, particularly under the extreme environmental conditions of interest, with a reasonable degree of accuracy.

SUMMARY OF THE INVENTION

The present invention overcomes the above-briefly discussed and other deficiencies and disadvantages of the prior art by providing a novel and improved technique for the testing, without human subjects, of footwear. The present invention also encompasses apparatus for use in the practice of the aforesaid method. In accordance with the present invention, the positions of the knee and ankle, and thus also the toes, for each portion of the walking movement of an individual are defined by means of a set of cams. A leg pylon and artificial foot, positioned by these cams, are articulated by a gearing system and the entire mechanism is mounted so that it may be raised and lowered between simulated steps under the control of a fluidic actuator. Pressure regulators are employed to control the rate of up-down movement at the beginning and end of each step and the downward walking force is adjustable so as to enable the simulation of individuals of different weight. The walking surface, i.e., the surface, the sole and heel of an article of footwear mounted on the artificial foot will contact, may be mounted on low-friction bearings and a transducer may be employed to measure the lateral walking forces generated.

The artificial foot of the apparatus of the present invention is a standard prosthetic foot which closely resembles the shape, texture and flexibility of the average human foot. This artificial foot is easily mounted on the leg pylon and is instrumented so as to enable the measurement of various parameters of interest and/or to simulate various boot internal conditions of interest.

Thus, the foot may be provided with means for detecting the exact time and location of moisture intrusion. Similarly, cold intrusion may be studied by embedding an array of thermocouples in the artificial foot. When it is desired to determine the caloric expenditure by the wearer required to keep the foot warm, the prosthetic foot affixed to the pylon may include both heater coils and thermocouples. In order to facilitate studies of the cushioning/shock absorbing characteristics of the footwear under test, a prosthetic foot of modified design is employed to more closely duplicate the rigid bone structure located in the heel of the human foot. When using this modified foot, an accelerometer is attached to the leg pylon assembly and the impact surface is adjusted to permit the boot/shoe to simulate different foot-strike positions.

Apparatus in accordance with the present invention may also include an environmental chamber which envelopes the walking surface of the test apparatus. This chamber may be equipped with a water tight observation window, which permits the operator to visually monitor the tests, and a removable, baffled cover used to prevent water splashed by a footwear from escaping the chamber. The chamber may be partly filled with water to study moisture permeability and may also be used for tests involving materials such as soil, mud and sand.

Another special chamber, which may be mounted on the test equipment, permits the evaluation of cold weather footwear. This additional chamber is heavily insulated and sealed at the top by a flexible, accordion fold, gauntlet which fits tightly over the leg pylon and permits the footwear under test to articulate within the chamber. The air within the chamber is circulated over thermostatically controlled refrigeration coils which permits testing at various low temperatures.

BRIEF DESCRIPTION OF THE DRAWING

The present invention may be better understood and its numerous objects and advantages will become apparent to those skilled in the art by reference to the accompanying drawing wherein like reference numerals refer to like elements in the several figures and in which:

FIG. 3 is a cross-sectional side elevation view of a second artificial foot which may be employed in the apparatus of FIG. 1;

FIG. 4 is a view taken along line 4—4 of FIG. 3;

DESCRIPTION OF THE PREFERRED EMBODIMENT

Figure 1:
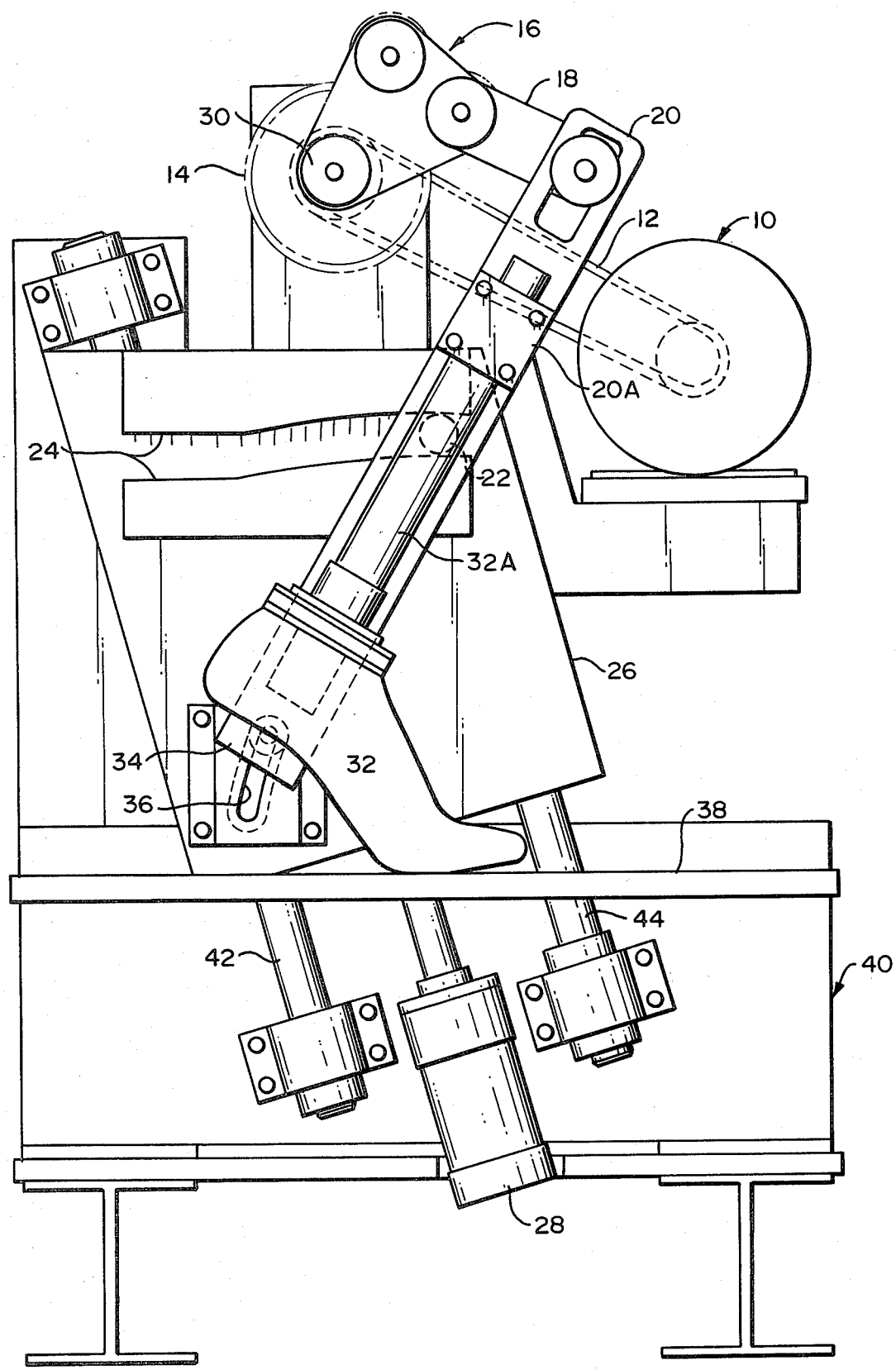
FIG. 1 is a side elevation view of a footwear testing apparatus in accordance with a preferred embodiment of the invention.

With reference now to the drawing, and especially to FIG. 1, the apparatus shown simulates the kinematic action of the toes, heel, ankle and knee of a person walking. The apparatus comprises a variable speed electric motor, indicated generally and schematically at 10, which can be adjusted to duplicate walking speeds between 2 and 4 mph. The output shaft of motor 10 is provided with a sprocket whereby the motor may drive, by means of a chain 12, another sprocket which is coupled to the rotating shaft 30 of a Cardan gear mechanism which has been indicated generally at 16. The Cardan gearing mechanism 16 rotates around the stationary gear 14 to convert rotary motion to linear motion and particularly to horizontal back and forth motion. The Cardan gearing mechanism 16 is coupled to the upper end of a cam bar 20 by means of a linkage 18 which is articulated to bar 20. The connection between linkage 18 and bar 20 permits straight line, horizontal, back and forth movement of the connection point.

The cam bar 20 is provided, intermediate its length, with a transversely extending cam follower 22 which moves forwardly and rearwardly in a cam track 24. The cam track 24 is mounted on the moveable plate 26 of the "walking mechanism". Up and down motion is imparted to plate 26 by means of a fluidic actuator 28 which may be an air cylinder. Air cylinder 28 is controlled by means of a double cam, not shown, mounted on the rotating shaft 30 about which the Cardan gearing mechanism 16 rotates.

A prosthetic foot, indicated generally at 32, and a leg pylon 32A are removably attached bar 20 so as to be moveable therewith. Leg pylon 32A is laterally offset from and parallel to bar 20. Bar 20 is provided, adjacent its lower end, with an "ankle" cam follower 34 which rides in a further cam slot 36. The means which defines cam slot 36 is affixed to plate 26 in any suitable manner. In actual use of the test apparatus, an article of footwear will be mounted on the prosthetic foot 32 and, during the simulated walking action, the test article will contact a stationary walking surface 38. Walking surface 38 will be affixed to the frame, indicated generally at 40, of the test apparatus. The first ends of a pair of parallel guide rods 42 and 44 are mounted on frame 40 below the simulated walking surface 38. These guide rods extend upwardly at an angle, as shown, and are secured at their upper ends to extensions of the frame 40. The walking mechanism, which includes the plate 26 and the means which defines the cam tracks 24 and 36, is slidably mounted on guide rods 42 and 44 for motion along the guide rods under control of the actuator 28.

In operation, at the walking speed determined by motor 10, the upper end or "knee" of the leg pylon 32A will be driven back and forth by reason of the rigid connection, part of which is indicated at 20A, between bar 20 and pylon 32A. During the forward motion the cooperation between the cam 22 and cam follower 24 will simulate the path of the knee while the cooperation between the cam follower 34 and cam 36 will simultaneously determine the location of the ankle. As cam 22 approaches the end of cam track 24, a first of the cams on shaft 30 will provide a signal which will cause actuator 28 to move the walking mechanism, particularly plate 26, upwardly away from the walking surface 38. During the backward motion of cam 22, as the cam reaches the other end of cam track 24, the second cam on shaft 30 will cause actuator 28 to be operated in the opposite direction whereupon plate 26 will descend and the article of footwear under test will again come into contact with walking surface 38. The flow of operating fluid to actuator 28 will be controllable whereby the force with which the article of footwear contacts walking surface 38 at the beginning of each step may be selected to simulate different body weights.

It is to be noted that analysis of motion picture film has proven that the motion of a leg/foot propelling an individual over moving terrain, i.e., a treadmill, is the same as that of a leg/foot articulating on stationary terrain such as the walking surface 38 of the test apparatus of FIG. 1. Thus, by defining all of the movements involved on the basis of a line drawn through the knee and ankle joints, it is possible to achieve all of the kinematic movement normal to walking without lateral displacement of the footwear. The necessary movements are embodied in the cams 24 and 36.

It is to be noted that the number of steps will typically be counted, for example by counting the cycling of the actuator 28, and elapsed time will also typically be recorded. It is further to be noted that the walking surface 38 may have various surface features and may be mounted on low-friction bearings, and associated with a transducer, whereby the lateral walking forces generated by different types of footwear may be measured.

Although not shown in the drawing, the test apparatus of FIG. 1 may be provided with an environmental chamber. This may, for example, be done by unbolting and lowering the walking surface 38 and then mounting the environmental chamber, having its own internal walking surface, on surface 38. In the case where the apparatus is to be employed for studing the moisture permeability of footwear the chamber will be a rectangular box, open at the top, which may have a water-tight observation window in the side thereof. The chamber will be partly filled with water during testing and will be provided with a removable, baffled cover. If the cold weather performance of footwear is to be tested, a heavily insulated chamber, sealed on the top by a flexible, accordion fold gauntlet which fits tightly around the leg pylon 20, will be supported on surface 38. The air within this insulated chamber will be circulated over thermostatically controlled refrigeration coils to permit testing at temperatures which, for example, may be in the range of +30° C. to −40° C. Similarly, a heated chamber may be placed on the walking surface to determine the performance of footwear under hot conditions.

Figure 2:
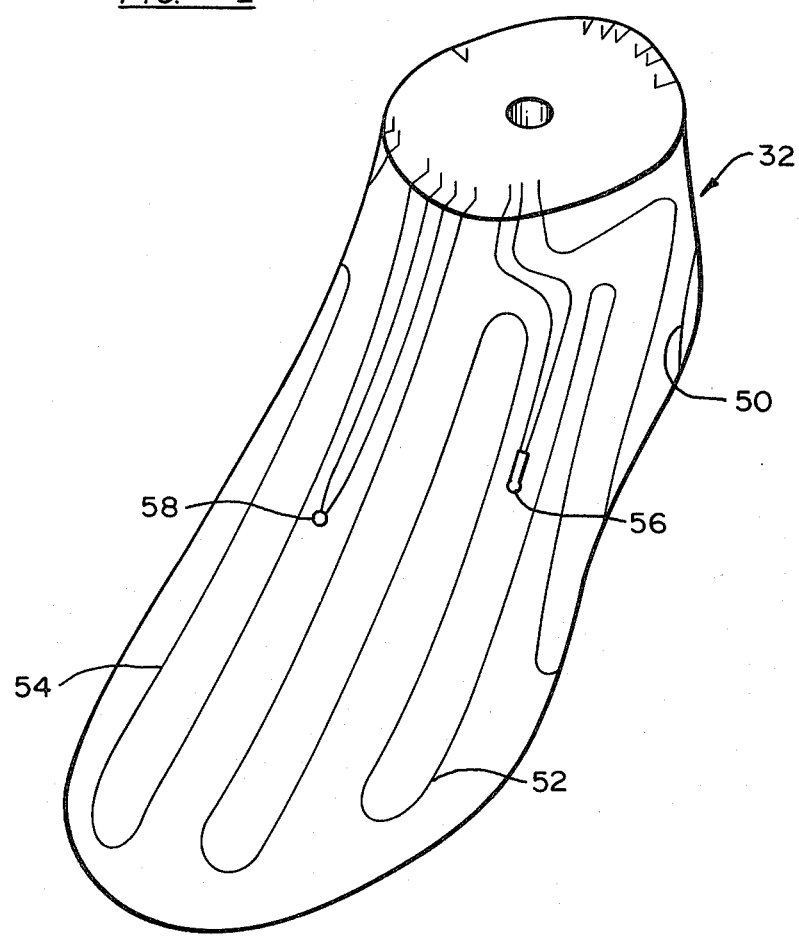
FIG. 2 is a perspective view of one artificial foot which may be employed in the apparatus of FIG. 1.

The prosthetic foot 32, which as noted above is removable from pylon 32A, may be instrumented to test or simulate one or a plurality of conditions. Thus, referring to FIG. 2, a "heated foot" is depicted. As noted above, the foot will comprise a standard prosthetic foot of the type used by amputees and thus will closely resemble the shape, texture and flexibility of the average human foot. However, the foot will be modified by implanting therein in those elements necessary to monitor or simulate the condition of interest. In the case of the heated foot, the prosthetic foot will be provided with slots in which various heaters and sensors are implanted, the implants subsequently being encapsulated by means of room temperature vulcanized silicone resin or other suitable flexible material. The foot of FIG. 2 includes a heel heater 50, an outer forefoot heater 52, an inner forefoot heater 54, an outer forefoot temperature sensor 56 which may, for example, comprise a thermister, an inner forefoot temperature control sensor, not shown, an overall temperature measuring thermocouple 58, a heel thermocouple, not shown, and a heel temperature control sensor, also not shown. The heaters 50, 52 and 54 are preferrably comprised of stainless steel heater coils. Through use of the heated foot of FIG. 2 the energy required to maintain each of the three zones, i.e., the right forefoot, left forefoot and heel, may be continuously measured and recorded while the footwear is subjected to varying temperatures. The energy consumed over a standard period of time, fifteen (15) minutes for example, may then be analysed to determine the caloric energy required to maintain the foot at a constant temperature.

Referring simultaneously to FIGS. 3 and 4, a foot employed for cushioning/shock absorbing testing is shown. The foot of FIGS. 3 and 4 is a version of the standard prosthetic foot which has been modified to more closely duplicate the very rigid bone structure located in the heel of the human foot. The foot of FIGS. 3 and 4 comprises a woden core 60 mounted on top of a rigid plastic instep defining member 62. A metal tube 64 will extend through member 62 and partly into the wooden member 60. Wooden member 60 will be provided with a through hole, as shown, which is coaxial with metal tube 64. The tube 64 and through hole permit the foot to be mounted on the leg pylon. The toe portion 66 of the foot of FIGS. 3 and 4 is comprised of hard rubber whereas the ball portion 68 and heel 70 are comprised of soft rubber foam. The foot of FIGS. 3 and 4 may be employed on the apparatus of FIG. 1 or it may be utilized on a modified version thereof which produces only motion along the guide rods 42 and 44. Thus, in testing the cushioning/shock absorbing characteristics of an article of footwear is it desirable to raise the prosthetic foot/leg pylon assembly to a given height where it will be held by any suitable means such as, for example, an electromagnet. Deenergization of the magnet will permit the walking mechanism to fall whereupon the boot or shoe being tested will strike the impact, i.e., walking, surface. An accelerometoer will be attached to the leg pylon assembly to measure the peak acceleration experienced by the prosthetic foot 32 during descent. It is desirable that the impact surface be adjustable to permit the boot/shoe to simulate different foot-strike positions. Also, rather than employ a fluidic actuator to control the force with which the boot/shoe strikes the surface, it is possible to add weight to the carriage and rely solely upon gravity. The accelerometer on the leg pylon will measure the change in acceleration when the shoe/boot strikes the impact or walking surface and this change in acceleration will be a measure of the cushioning effect of the footwear article.

Figure 5:
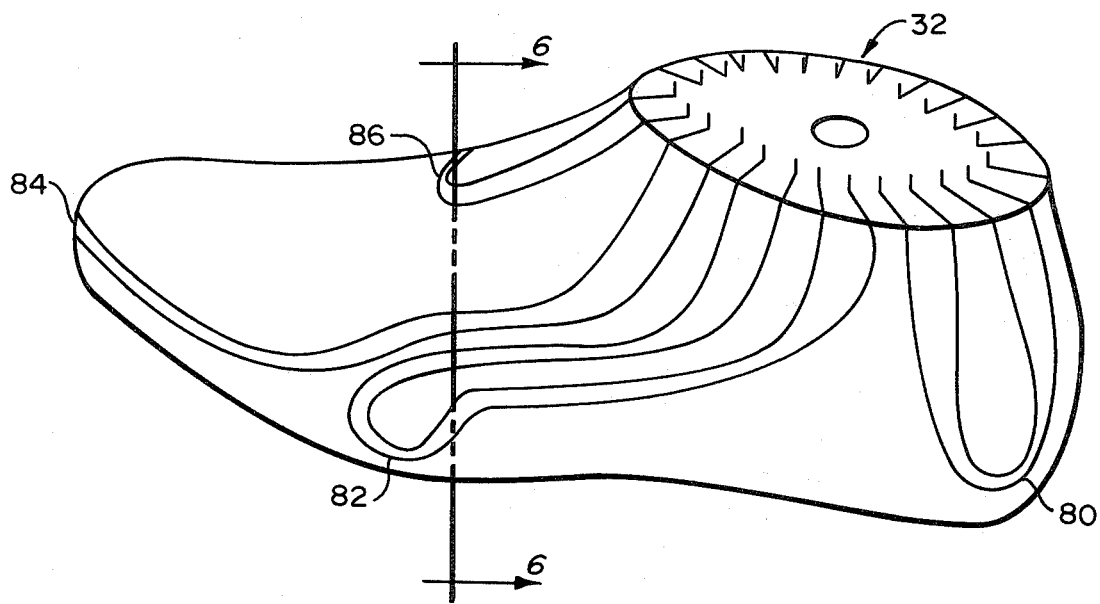
FIG. 5 is a perspective view of a third artificial foot which may be employed in the apparatus of FIG. 1.
Figure 6:
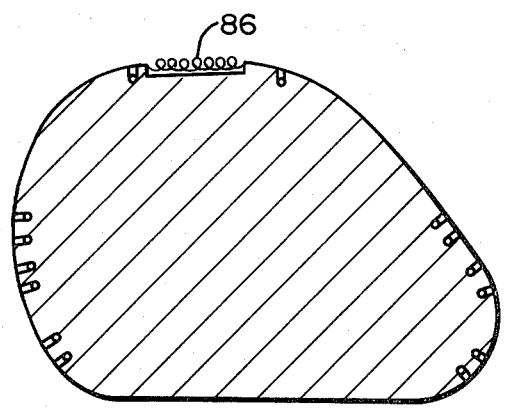
FIG. 6 is a view taken along line 6—6 of FIG. 5.

FIGS. 5 and 6 depict yet another foot which may be installed on the leg pylon 20 of the apparatus of FIG. 1. The foot of FIGS. 5 and 6 is specifically designed to detect moisture intrusion and determine the exact time and location thereof. The foot 32 is provided with an array of sensors positioned in the locations where information is desired such as, for example, the big toe, inner and outer ball, instep and inner and outer heel. Each sensor consists of a pair of parallel stainless steel wires which are embedded in the foot with short adjacent sections of each pair of sensors being exposed in the areas to be sampled. When moisture completes the electrical circuit between the adjacent sensor elements, a signal will be generated which may be recorded. Thus, in the foot of FIGS. 5 and 6 the outer heel sensor is indicated at 80, the outer ball sensor is indicated a 82, the toe sensor is indicated at 84 and the instep sensor is indicated at 86.

Referring to FIG. 6, while they can not be seen as such in FIG. 5 because of the scale of the drawing, the actual exposed portions of the moisture sensors are in the form of spring-like coils wound from stainless steel wire. The wire may, for example, have a diameter of 0.012" and the coils may have a diameter of 0.086". The use of such stainless steel coils is dictated by the fact that the flexing to which the prosthetic feet are subjected during simulated walking produces an extremely hostile environment for the implanted leads and sensors. Additionally, when conducting a moisture test, in the interest of increased conductivity of the water, salt will customarily be added thereto and this salt water has a strongly corrosive effect on most types of wires. In actual practice, even when using stainless steel coils, the coils are passivated with nitric acid to increase their resistance to corrosion.

While preferred embodiments have been shown and described, various modifications and substitutions may be made thereto without departing from the spirit and scope of the invention. Thus, by way of example, of foot with a plurality of embedded thermocouples may be employed to measure the resistance to cold intrusion of a particular article of footwear. Also, a prosthetic foot with porous tubes embedded in the surface thereof dispense water, salt solution , etc. may be employed to determine the effect of perspiration on boots/shoes. Accordingly, it will be understood that the present invention has been described by way of illustration and not limitation.

What is claimed is:

1. Apparatus for simulating terrain traversing movements of a human foot comprising:
   artificial foot means;
   a platform, said platform having a generally planar upper surface;
   elongated leg pylon means, said foot means being attached to said pylon means adjacent a first end thereof;
   first means for imparting motion to said pylon means, said first motion imparting means being coupled to said pylon means at a point displaced from said simulated foot;
   second means for imparting motion to said pylon means;
   first cam means, said first cam means including a cam track and cam follower, said first cam means coupling said second motion imparting means to said pylon means a point intermediate the ends thereof, the direction of motion of said pylon means second end resulting from operation of said first motion imparting means being determined by said first cam means and said second motion imparting means, the motion of said pylon means second end simulating the action of the human knee; and
   second cam means, said second cam means including a cam track and cam follower, said second cam means coupling said second motion imparting means to said pylon means adjacent the first end thereof, the motion of said foot means relative to said platform being determined by said second cam means in response to operation of said first and second motion imparting means, said second cam means simulating the action of the human ankle.

2. The apparatus of claim 1 wherein said second motion imparting means comprises:
   movable plate means, the cam track defining means of said cam means being affixed to said plate means;
   means for producing motion of said plate means; and
   guide means for directing the motion of said plate means, said guide means defining a path of movement including a component angularly related to said platform means planar surface whereby said foot means will be moved toward and away from said surface by the operation of said plate means motion producing means.

3. The apparatus of claim 1 wherein said first motion imparting means comprises:
   motor means, said motor means having a rotatable output shaft;
   means coupled to said motor means output shaft for translating rotary motion thereof to linear motion; and
   means coupling said motion translating means to said pylon means adjacent the second end thereof, said translating and coupling means being oriented to produce motion of said pylon means second end which is generally in direction parallel to said platform upper surface.

4. The apparatus of claim 2 wherein said first motion imparting means comprises:
   motor means, said motor means having a rotatable output shaft;
   means coupled to said motor means output shaft for translating rotary motion thereof to linear motion; and
   means coupling said motion translating means to said pylon means adjacent the second end thereof, said translating and coupling means being oriented to produce motion of said pylon means second end which is generally in direction parallel to said platform upper surface.

5. The apparatus of claim 4 wherein said second cam means cam track defines an accurate path.

6. The apparatus of claim 5 wherein said guide means defines a linear path.

7. The apparatus of claim 6 wherein said pylon means comprises:
   a cam bar, said coupling means being connected to said cam bar; said cam means cam followers being affixed to said cam bar;
   a rod;
   means for detachably mounting said foot means on a first end of said rod; and
   means for supporting said rod on said cam bar.

8. The apparatus of claims 1–7 wherein an article of anyone of footwear may be tested by mounting on said foot means, and wherein said foot means comprises:
   a prosthetic foot, said foot including at least a first electric heater implanted therein.

9. The apparatus of claims 1–7 wherein an article of anyone of footwear may be tested by mounting on said foot means, and wherein said foot means comprises:
   a prosthetic foot, said foot including at least a first moisture responsive sensor mounted thereon.

10. The apparatus of claims 1–7 wherein an article of anyone of footwear may be tested by mounting on said foot means, and wherein said foot means comprises:
    a prosthetic foot, said foot comprising a rigid core and instep defining means, mounting means extending through said core and instep defining means for engagement by said pylon means, resilient heel and ball defining means affixed to said core and instep defining means, and means defining a toe and top portion.

* * * * *